(12) United States Patent
Simpson

(10) Patent No.: US 9,061,088 B2
(45) Date of Patent: Jun. 23, 2015

(54) GUIDE WIRE CORE WIRE MADE FROM A SUBSTANTIALLY TITANIUM-FREE ALLOY FOR ENHANCED GUIDE WIRE STEERING RESPONSE

(75) Inventor: John A. Simpson, Carlsbad, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 434 days.

(21) Appl. No.: 13/364,548

(22) Filed: Feb. 2, 2012

(65) Prior Publication Data
US 2013/0204163 A1 Aug. 8, 2013

(51) Int. Cl.
| | |
|---|---|
| A61B 5/00 | (2006.01) |
| A61M 25/00 | (2006.01) |
| A61L 29/02 | (2006.01) |
| A61L 31/02 | (2006.01) |
| A61L 31/14 | (2006.01) |
| A61F 2/95 | (2013.01) |
| A61M 25/09 | (2006.01) |

(Continued)

(52) U.S. Cl.
CPC ............ *A61L 29/02* (2013.01); *Y10T 29/49826* (2015.01); *A61L 31/022* (2013.01); *A61L 31/14* (2013.01); *A61F 2/95* (2013.01); *A61M 25/09* (2013.01); *C21D 7/00* (2013.01); *A61M 2025/09108* (2013.01); *A61M 2025/09133* (2013.01); *C22C 19/055* (2013.01); *C22C 19/056* (2013.01); *C22C 19/07* (2013.01); *C22F 1/10* (2013.01)

(58) Field of Classification Search
CPC ...... A61M 25/09; A61M 25/00; B21D 39/03; A61B 5/00
USPC ...................... 600/585, 433–435; 604/164.13
See application file for complete search history.

(56) References Cited

U.S. PATENT DOCUMENTS

| | | | |
|---|---|---|---|
| 4,358,658 A | 11/1982 | Van Blarigan et al. | |
| 4,518,444 A | 5/1985 | Albrecht et al. | |

(Continued)

FOREIGN PATENT DOCUMENTS

| | | |
|---|---|---|
| EP | 1388350 | 2/2004 |
| GB | 1552165 | 9/1979 |

(Continued)

OTHER PUBLICATIONS http://wilcowirelines.com/documents/Products/Zapp/Alloy%20MP35N%20e_09%2009%20USA.pdf Please Note: (The PDF is also saved as: Alloy-MP35N-e_USA_01-13.pdf).*

(Continued)

*Primary Examiner* — Brian Szmal
(74) *Attorney, Agent, or Firm* — Workman Nydegger; John Kwok

(57) ABSTRACT

Guide wire devices and methods for their manufacture. Guide wire devices include an elongate guide wire member that includes at least one section fabricated from a substantially titanium-free Co—Ni—Cr—Mo alloy. The substantially titanium-free Co—Ni—Cr—Mo alloy exhibits superior stiffness (i.e., greater Young's and shear moduli) as compared to stainless steel (e.g., 304V stainless steel) and nickel-titanium (Ni—Ti) and a greater yield strength as compared to stainless steel. Increasing the Young's and shear moduli can significantly improve torque transmission and steerability of the guide wire device and increasing the yield strength can significantly improve the kink resistance of the guide wire device.

14 Claims, 2 Drawing Sheets

(51) Int. Cl.

| | |
|---|---|
| *C21D 7/00* | (2006.01) |
| *C22C 19/05* | (2006.01) |
| *C22C 19/07* | (2006.01) |
| *C22F 1/10* | (2006.01) |

(56) References Cited

U.S. PATENT DOCUMENTS

| | | | |
|---|---|---|---|
| 4,922,924 A * | 5/1990 | Gambale et al. | 600/585 |
| 5,124,529 A | 6/1992 | Nishikawa et al. | |
| 5,135,503 A | 8/1992 | Abrams | |
| 5,354,623 A | 10/1994 | Hall | |
| 5,368,661 A | 11/1994 | Nakamura et al. | |
| 5,411,476 A | 5/1995 | Abrams et al. | |
| 5,415,178 A * | 5/1995 | Hsi et al. | 600/585 |
| 5,488,959 A | 2/1996 | Ales | |
| 5,630,840 A * | 5/1997 | Mayer | 623/66.1 |
| 5,720,300 A * | 2/1998 | Fagan et al. | 600/585 |
| 5,876,783 A * | 3/1999 | Dobson | 427/2.12 |
| 5,951,886 A | 9/1999 | Schubert et al. | |
| 6,248,082 B1 | 6/2001 | Jafari | |
| 6,267,776 B1 * | 7/2001 | O'Connell | 606/200 |
| 6,306,105 B1 | 10/2001 | Rooney et al. | |
| 6,379,392 B1 | 4/2002 | Walak | |
| 6,387,060 B1 | 5/2002 | Jalisi | |
| 6,602,208 B2 | 8/2003 | Jafari | |
| 6,645,159 B1 | 11/2003 | Burkett | |
| 6,669,652 B2 | 12/2003 | Anderson et al. | |
| 6,702,762 B2 | 3/2004 | Jafari | |
| 6,729,526 B2 | 5/2004 | Okamoto et al. | |
| 6,736,843 B1 | 5/2004 | Fariabi | |
| 6,866,642 B2 | 3/2005 | Kellerman et al. | |
| 6,918,882 B2 | 7/2005 | Skujins et al. | |
| 7,316,656 B2 | 1/2008 | Shireman et al. | |
| 7,547,288 B2 | 6/2009 | Murayama et al. | |
| 7,632,237 B2 | 12/2009 | Murayama et al. | |
| 7,722,552 B2 * | 5/2010 | Aimi et al. | 600/585 |
| 7,785,273 B2 * | 8/2010 | Eskuri | 600/585 |
| 7,785,274 B2 * | 8/2010 | Mishima et al. | 600/585 |
| 7,998,090 B2 * | 8/2011 | Simpson et al. | 600/585 |
| 2002/0179202 A1 | 12/2002 | Kautz et al. | |
| 2003/0220677 A1 * | 11/2003 | Doan et al. | 607/122 |
| 2004/0030265 A1 | 2/2004 | Murayama et al. | |
| 2004/0039309 A1 | 2/2004 | Murayama et al. | |
| 2004/0167442 A1 | 8/2004 | Shireman et al. | |
| 2004/0167443 A1 | 8/2004 | Shireman et al. | |
| 2004/0181176 A1 | 9/2004 | Jafari et al. | |
| 2004/0260206 A1 | 12/2004 | Murayama et al. | |
| 2005/0051243 A1 * | 3/2005 | Forbes Jones et al. | 148/442 |
| 2005/0137501 A1 | 6/2005 | Euteneuer et al. | |
| 2006/0047223 A1 | 3/2006 | Grandfield et al. | |
| 2006/0259063 A1 * | 11/2006 | Bates et al. | 606/198 |
| 2007/0010762 A1 * | 1/2007 | Ressemann et al. | 600/585 |
| 2007/0199607 A1 | 8/2007 | Murayama et al. | |
| 2007/0244413 A1 * | 10/2007 | Biggins | 600/585 |
| 2008/0171952 A1 | 7/2008 | Mishima | |
| 2009/0318835 A1 * | 12/2009 | Ressemann et al. | 600/585 |
| 2010/0075168 A1 | 3/2010 | Schaffer | |
| 2010/0119870 A1 | 5/2010 | Nojiri et al. | |
| 2011/0278264 A1 | 11/2011 | Murayama et al. | |
| 2011/0295155 A1 | 12/2011 | Simpson et al. | |
| 2012/0228273 A1 | 9/2012 | Mishima et al. | |
| 2012/0305533 A1 | 12/2012 | Matteson | |
| 2014/0200555 A1 | 7/2014 | Simpson et al. | |

FOREIGN PATENT DOCUMENTS

| | | |
|---|---|---|
| JP | 2004-292174 | 10/1992 |
| JP | 2003-190291 | 7/2003 |
| JP | 2004-065797 | 3/2004 |
| WO | WO 03/057273 | 7/2003 |
| WO | WO 2004/033016 | 4/2004 |
| WO | WO 2008/123402 | 10/2008 |
| WO | WO 2013/116379 | 8/2013 |

OTHER PUBLICATIONS

Fort Wayne Metals, Research Products Corp., 2011, pp. 1-43.*
http://www.zapp.com/fileadmin/downloads/01-Produkte/Oel-und-Gas/Alloy-MP35N-e_USA_01-13.pdf, 2014.*
U.S. Appl. No. 13/744,276, filed Jan. 17, 2013, Simpson et al.
DC25/UB25 Linear DC Welding Controls, Brochure, Miyachi Unitek Corporation, (2011).
EWI, "EWI's Nitinol-Stainless Steel Welding Process Enables More Advanced Applications of Shape Memory Alloys," Insights Materials Joining Newsletter, p. 6, Winter 2004, vol. 17, No. 1.
Ryhanen, J., "Fundamental chracteristics of nickel—titanium shape memory alloy," *Biocampatibility Evaluation of Nickel—titanium Shape memory Metal Alloy*, Academic Dissertation presented at University Hospital of Oulu, May 7, 1999, pp. 24-31.
Improving Resistance Welding Process Control in Medical Applications, *MDDI Medical Device and Diagnostic Industry Magazine*, Nov. 1, 1997, p. 1-9.
MEA-100 AC Resistance Welding Power Supply, Technical Data Sheet, Miyachi Europe Corporation, Jul. 2012, pp. 1-3.
Wang, G., "Welding of Nitinol to Stainless Steel," Proceedings of the second International Conference on Shape Memory and Superelastic Technologies, 1996, p. 131-136, Asilomar Conference Center, Pacific Grove, California.

* cited by examiner

GUIDE WIRE CORE WIRE MADE FROM A SUBSTANTIALLY TITANIUM-FREE ALLOY FOR ENHANCED GUIDE WIRE STEERING RESPONSE

BACKGROUND

Guide wires are used to guide a catheter for treatment of intravascular sites such as Percutaneous Transluminal Coronary Angioplasty ("PTCA"), or in examination such as cardio-angiography. For example, a guide wire used in the PTCA is inserted into the vicinity of a target angiostenosis portion together with a balloon catheter, and is operated to guide the distal end portion of the balloon catheter to the target angiostenosis portion.

In order to facilitate guiding a guide wire through a patient's vascular anatomy (e.g., from an exterior access point to an intravascular treatment site), a guide wire needs to meet a number of performance criteria. For example, a guide wire needs appropriate flexibility, pushability and torque transmission performance for transmitting an operational force from the proximal end portion to the distal end, and kink resistance (resistance against sharp bending).

BRIEF SUMMARY

The present disclosure describes guide wire devices and methods for their manufacture. The guide wire devices described in the present disclosure include an elongate guide wire member that includes at least one section fabricated from a substantially titanium-free Co—Ni—Cr—Mo alloy. The substantially titanium-free Co—Ni—Cr—Mo alloy, which goes by the names MP35NLT® and 35N LT®, exhibits superior stiffness (i.e., greater Young's and shear moduli) as compared to stainless steel (e.g., 304V stainless steel) and nickel-titanium (Ni—Ti) and a greater yield strength as compared to stainless steel. Increasing the Young's and shear moduli can significantly improve torque transmission and steerability of the guide wire device and increasing the yield strength can significantly improve the kink resistance of the guide wire device.

In one embodiment, a guide wire device is described. The guide wire device includes an elongate guide wire member having a proximal end section and a distal end section, wherein at least one of the proximal end section or the distal end section of the elongate guide wire member is fabricated from a cobalt-nickel-chromium-molybdenum (Co—Ni—Cr—Mo) alloy that is substantially free of titanium (e.g., less than about 0.05% titanium by weight).

In another embodiment, a guide wire device includes an elongate guide wire member having a proximal end section and a distal end section, wherein at least one of the proximal end section or the distal end section of the elongate guide wire member is fabricated from a substantially titanium-free Co—Ni—Cr—Mo alloy having a Young's modulus of at least about 230 GPa, a shear modulus of at least about 80 GPa, and a yield strength of about 1 GPa to about 2 GPa. The Young's modulus and the shear modulus of the Co—Ni—Cr—Mo alloy used to fabricate the guide wire device are higher than stainless steel and significantly higher than either austentic or martensitic Ni—Ti. The yield strength is significantly higher that stainless steel. Wire diameter profile, the Young's modulus, and shear modulus are reasonable predictors of torque transmission and catheter support provided by a guide wire device, whereas yield strength is a reasonable predictor of its kink resistance.

In yet another embodiment, a method for fabricating a guide wire device is disclosed. The method includes (1) fabricating an elongate guide wire member having a proximal section and a distal section, wherein at one of the proximal section or the distal section is fabricated from a Co—Ni—Cr—Mo alloy that is substantially free of titanium and (2) grinding the distal end section to a distally tapered cross sectional diameter of about 0.3 mm to about 0.05 mm. The method further includes (3) disposing a helical coil section about at least a distal end portion of the distal section, (4) joining the helical coil to the elongate guide wire member at a proximal location, (5) forming a rounded cap section on a distal end of the helical coil, and (6) applying at least one lubricious outer coating layer over at least a portion of the elongate guide wire member to form the guide wire device.

In some embodiments of the guide wire device and methods disclosed herein, the proximal end section is fabricated from a stainless steel alloy (e.g., 304V or 316L stainless steel), the distal end section is fabricated from the Co—Ni—Cr—Mo alloy, and the proximal end section and the distal end section are joined to one another by one or more of a welded joint, a brazed joint, or an adhesive joint. In another aspect of the guide wire devices and methods disclosed herein, the proximal end section and the distal end section are fabricated from the Co—Ni—Cr—Mo alloy. In yet another aspect, the proximal section is the Co—Ni—Cr—Mo alloy and the distal section is superelastic or linear elastic nitinol.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. The present disclosure will be described and explained with additional specificity and detail through the use of the accompanying drawings in which.

DETAILED DESCRIPTION

I. Introduction

Figure 1:
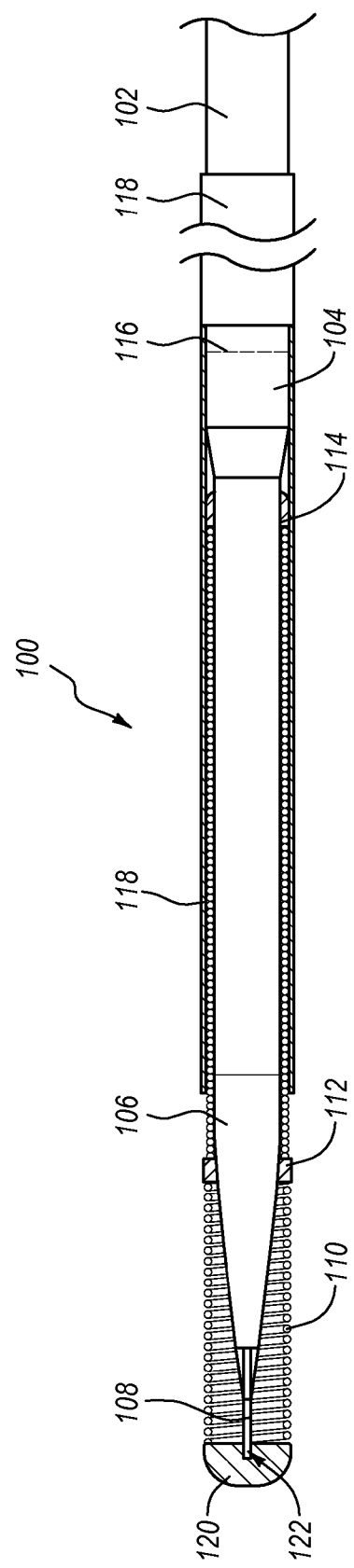
FIG. 1 illustrates a partial cut-away view of a guide wire device according to one embodiment of the present invention.

The present disclosure describes guide wire devices and methods for their manufacture. The guide wire devices described in the present disclosure include an elongate guide wire member that includes at least one section fabricated from a substantially titanium-free Co—Ni—Cr—Mo alloy. The substantially titanium-free Co—Ni—Cr—Mo alloy, which goes by the names MP35NLT® or 35N LT®, exhibits superior stiffness (i.e., greater Young's and shear moduli) as compared to stainless steel (e.g., 304V stainless steel) and nickel-titanium and a greater yield strength as compared to stainless steel. Increasing the Young's and shear moduli can significantly improve torque transmission and steerability of the guide wire device and increasing the yield strength can significantly improve the kink resistance of the guide wire device.

Because guide wire devices are designed to track through a patient's vasculature, for example, guide wire devices may be quite long (e.g., about 150 cm to about 300 cm in length) and thin. Guide wire devices need to be long enough to travel from an access point outside a patient's body to a treatment site and narrow enough to pass freely through the patient's vasculature. For example, a typical guide wire device has an overall diameter of about 0.2 mm to about 0.5 mm for coronary use. Larger diameter guide wires may be employed in peripheral arteries and other body lumens. The diameter of the guide wire device affects its flexibility, support, and torque. Thinner wires are more flexible and are able to access narrower vessels while larger diameter wires offer greater support and torque transmission.

Some typical examples of guide wire devices are constructed with a superelastic Ni—Ti alloy core wire, a two part wire that includes a binary Ni—Ti distal core section welded, brazed, or otherwise joined to a stainless steel proximal core section, and so-called all-stainless steel "core to tip" guide wire designs.

Superelastic Ni—Ti alloys are noted for their flexibility and extreme kink resistance, but Ni—Ti core wires can be more difficult to manipulate when a high level of torque transmission is needed. Despite the advantages of a superelastic Ni—Ti guide wire core (e.g., the ability to bend quite dramatically without causing permanent deformation), typical Ni—Ti guide wires generally do not transmit applied torque as effectively from the proximal shaft because the shear modulus and the Young's modulus of Ni—Ti alloy are substantially lower than those of stainless steel. As a result, superelastic Ni—Ti tends to "wind up" or store twist as opposed to transmitting torque directly from end-to-end. One way to increase the bending and torsional stiffness of a guide wire core wire is to increase its diameter. Nevertheless, the diameter of a core wire is limited by the design specifications of the guide wire, which in turn are limited by the lumen size of those catheters with which the guide wire is intended to be used. While the distal grind profiles of superelastic Ni—Ti core wires are typically larger than those of stainless steel, there is an inherent limit to the torque transmission that can be obtained with superelastic Ni—Ti core wires without exceeding product dimensional requirements.

In contrast to Ni—Ti, stainless steel alloys are desired in many applications because of their stiffness and torqueability. Stainless steel guide wire cores are presently made from grades of stainless steel such as 316L or 304V. Stainless steel is far stiffer than Ni—Ti and it is thus easier to steer through a patient's vasculature because torque is well transmitted from the proximal end to the distal end of a wire. As a result, stainless steel guide wire cores can generally be made thinner than comparable Ni—Ti core wires. However, while stainless steel "core to tip" guide wires can be made much thinner than Ni—Ti wires, stainless steel is much more likely to kink when the wire is prolapsed or when guiding through tortuous anatomy. If kinking occurs, guide wire performance is often substantially reduced due to "whipping," in which elastic windup builds within the section proximal to the kink until sufficient torque causes the kinked region to abruptly rotate one complete revolution. This behavior makes delicate manipulation of the guide wire's distal end difficult, if not impossible.

In contrast to either Ni—Ti or stainless steel, the present disclosure relates to the use of a substantially titanium-free cobalt-nickel-chromium-molybdenum (Co—Ni—Cr—Mo) alloy material (known as MP35NLT or 35N LT®) that exhibits a superior stiffness (i.e., greater Young's and shear moduli) as compared to commonly used stainless steels and Ni—Ti and a greater yield strength as compared to stainless steel. Such a material exhibits many of the best properties of stainless steel and Ni—Ti, without the drawbacks. For example, due to its higher Young's and shear moduli, such a material would be expected to exhibit improved steering response as compared to Ni—Ti and, to a lesser degree, stainless steel because steering forces are more likely to be transferred directly along the length of the guide wire. Likewise, while MP35NLT can be torqued and steered even better than stainless steel, it is expected to be less likely to kink due to its higher yield strength.

Tables 1-3 illustrate some of the physical properties of MP35NLT as compared to Ni—Ti alloy and stainless steel.

TABLE 1

| Young's Modulus (GPa) | |
| --- | --- |
| MP35NLT | ~232-235 |
| 304V Stainless Steel | ~193-200 |
| Ni—Ti (austenite) | 82 |
| Ni—Ti (martensite) | 30 |

TABLE 2

| Shear Modulus (GPa) | |
| --- | --- |
| MP35NLT | ~80-84 |
| 304V Stainless Steel | ~69-73 |
| Ni—Ti (superelastic) | ~24 |

To a first approximation, the Young's modulus and the shear modulus (as reported in gigaPascals or "GPa") are measures of tensile and torsional stiffness of a material, respectively. In general, a material with higher Young's and shear moduli will be easier to steer through a patient's anatomy because the material will transfer torque applied at the proximal end to the distal end as opposed to building significant elastic windup. As can be seen from Tables 1 and 2, MP35NLT has Young's and shear moduli that are comparable to but higher than 304V and considerably higher than Ni—Ti. In general, a guide wire having a core wire made of MP35NLT should be easier to steer through a patient's anatomy because the material will transfer torque applied at the proximal end to the distal more efficiently than either stainless steel or Ni—Ti.

Table 3 (below) illustrates the yield strength of MP35NLT as compared to 304V stainless steel. The yield strength or yield point of a material is defined as the stress (as reported in GPa) at which a material begins to deform plastically. Prior to the yield point the material will deform elastically in response to an applied stress and, rather than permanently kinking, will return to its original shape when the applied stress is removed. Once the yield point is passed, however, some fraction of the deformation will be permanent and non-reversible.

As can be seen from the data presented in Table 3, MP35NLT has a higher yield strength than 304V stainless steel at all cold work levels. As such, a guide wire core wire fabricated from MP35NLT will be able to tolerate more severe bending stresses while navigating tortuous anatomy without permanently deforming, as compared to stainless steel. MP35NLT is not as kink resistant as Ni—Ti, but MP35NLT has greater bending and torsional stiffness that makes it more desirable than superelastic Ni—Ti in many applications.

TABLE 3

YIELD STRENGTH (GPa)

| % Cold Work | MP35NLT | 304V Stainless Steel |
|---|---|---|
| 0 | 0.90 | 0.35 |
| 20 | 1.31 | 0.48 |
| 37 | 1.66 | 0.62 |
| 50 | 1.86 | 0.97 |
| 60 | 2.00 | 1.10 |
| 68 | 2.07 | 1.24 |
| 75 | 2.10 | 1.38 |
| 80 | 2.17 | 1.48 |
| 84 | 2.24 | 1.59 |
| 90 | 2.30 | 1.69 |
| 93 | 2.33 | 1.72 |
| 95 | 2.34 | 1.93 |

The substantially titanium-free Co—Ni—Cr—Mo alloy disclosed herein (i.e., MP35NLT) is a nickel-cobalt-based alloy that has a face-centered cubic matrix of cobalt and nickel in which chromium and molybdenum are soluble at elevated temperatures. The face-centered cubic structure persists upon cooling to room-temperature and below.

Conventionally prepared MP35N alloy includes up to about 1% titanium as a deliberate additional alloying element. It is believed that the addition of titanium may provide the alloy with properties that are favored by manufacturers of some articles. However, titanium has a strong tendency to form carbides and nitrides as a result of exposure to carbon and nitrogen during melting procedures. The resulting carbide and nitride inclusions can reduce the fatigue life of the wires used for guide wire cores. For example, the titanium carbide and nitride inclusions are brittle and non-malleable, which is in contrast to the properties of the bulk Co—Ni—Cr—Mo material, and, as such, they can act as origins for crack formation of the fine wires used for guide wire cores.

By reducing the titanium to an extremely low level (e.g., less than 0.05 wt %), the size and overall quantity of titanium carbide and titanium nitride inclusions can be substantially reduced (e.g., from about 550,000 inclusions per square inch for conventional MP35N to about 35,000 inclusion per square inch for MP35NLT). Such reductions on the numbers of inclusions can significantly reduce the likelihood of breakage of a guide wire core wire as a result of the torquing and bending forces experienced by a guide wire while traversing a patient's anatomy.

In one embodiment, the substantially titanium-free Co—Ni—Cr—Mo alloy (i.e., MP35NLT) disclosed herein includes about 31.5 wt % to about 39 wt % cobalt, about 33 wt % to about 37 wt % nickel, about 19 wt % to about 21 wt % chromium, about 9 wt % to about 10.5 wt % molybdenum, and less than about 0.05 wt % titanium. In another embodiment, the MP35NLT alloy disclosed herein includes about 35 wt % cobalt, about 35 wt % nickel, about 20.5 wt % chromium, about 9.5 wt % molybdenum, and less than about 0.05 wt % titanium. Preferably, the MP35NLT contains less than about 0.01 wt % titanium, less than about 0.005 wt % titanium, or less than about 0.001 wt % titanium.

To form a substantially titanium-free Co—Ni—Cr—Mo alloy, each of the four principal elements (i.e., cobalt, nickel, chromium, and molybdenum) can be refined to form a furnace charge stock that is substantially free of titanium and other contaminating elements. The refined principal elements are combined in an alloy melt by vacuum induction melting. Homogenization and final refining is performed in a vacuum arc remelt furnace. The Co—Ni—Cr—Mo alloy material produced in this way typically contains less than 0.05 wt % titanium, less than about 0.01 wt % titanium, less than about 0.005 wt % titanium, or less than about 0.001 wt % titanium in comparison to conventionally processed MP35N, which deliberately contains up to 1.0% titanium by weight.

After vacuum arc refining and cooling, MP35NLT can be processed into wire for forming a guide wire core by conventional cold processing methods including one or more of drawing, swaging, cold rolling, stamping, extrusion, forging, or other suitable cold processing methods. Cold working the MP35NLT alloy using processes such as those listed herein can yield significant increases in strength (see, e.g., Table 3). In one embodiment, the MP35NLT alloy has a yield strength of about 1 GPa to about 2.3 GPa imparted by at least about 10% to about 95% cold work, about 10% to about 60% cold work, or about 20% to about 50% cold work.

For further increases in yield strength, cold worked MP35N or MP35NLT alloy can be age hardened by heat treating the alloy at a temperature of at least about 430° C. to about 650° C. for about 30 minutes to about 240 minutes. Such heat treatment serves to strengthen the alloy by stabilizing the dislocation structure produced during cold work. While age hardening thermal treatments are used in a variety of alloy systems in order to cause the formation of very fine precipitate particles that hinder dislocation movement and thereby increase strength with only moderate impact on ductility, the metallurgical reaction which occurs in MP35N and MP35NLT involves another mechanism, the organization and stabilization of stacking faults. At the high levels of prior cold work needed to provide high yield strengths in guide wire applications, deliberate age hardening of MP35N or MP35NLT can lead to severe loss of ductility and is thus not generally recommended.

II. Guide Wire Devices

As discussed in greater detail elsewhere herein, guide wire devices are typically made from stainless steel, a conventionally processed superelastic Ni—Ti alloy, or a combination of the two. For a given wire diameter, stainless steel is quite a bit stiffer than superelastic Ni—Ti and is generally better at transmitting torque. Nevertheless, stainless steel is susceptible to kinking while passing through tortuous anatomy. In contrast, superelastic Ni—Ti is much less susceptible to kinking but it is not effective for transmitting torque.

In ordinary applications, differences in flexibility between two materials can be readily compensated for by dimensional alterations. That is, for example, the tendency to wind up that is typical of conventionally processed superelastic Ni—Ti can ordinarily be compensated for by increasing the diameter of the wire in order to attain equivalent deflection behavior when compared to a stiffer wire material. However, guide wire devices typically face inherent dimensional constraints that are imposed by the overall product profile, by the allowable space within overlying coils or polymeric jacketing, and/or the size of the anatomy to be accessed. For this reason, use of substantially titanium-free Co—Ni—Cr—Mo alloys exhibiting superior stiffness (i.e., greater Young's and shear moduli) and a greater yield strength significantly expand the maximum range of torsional or bending stiffness that can be achieved in a guide wire of a given profile.

In one embodiment, a guide wire device includes an elongate guide wire member having a proximal section and a distal section. At least a portion of the elongate guide wire member is fabricated from a cobalt-nickel-chromium-molybdenum (Co—Ni—Cr—Mo) alloy that is substantially free of titanium (e.g., less than about 0.05% titanium by weight).

In another embodiment, a guide wire device includes an elongate guide wire member having a proximal end section and a distal end section, wherein at least one of the proximal end section or the distal end section of the elongate guide wire member is fabricated from a substantially titanium-free Co—Ni—Cr—Mo alloy having a Young's modulus of at least about 230 GPa, a shear modulus of at least about 80 GPa, and a yield strength of about 1 GPa to about 2 GPa. The Young's modulus and the shear modulus of the Co—Ni—Cr—Mo alloy used to fabricate the guide wire device are higher than stainless steel and significantly higher than either austentic or martensitic Ni—Ti. The yield strength is significantly higher than stainless steel. The Young's and shear moduli are a reasonable predictor of navigability of a guide wire device and yield strength is a reasonable predictor of kink resistance of a guide wire device.

Referring now to FIG. 1, a partial cut-away view of an example of a guide wire device 100 is illustrated. The guide wire device 100 may be adapted to be inserted into a patient's body lumen, such as an artery or another blood vessel. The guide wire device 100 includes an elongated proximal portion 102 and a distal portion 104. In one embodiment, both the elongated proximal portion 102 and the distal portion 104 may be formed from any of the substantially titanium-free Co—Ni—Cr—Mo alloys disclosed herein. In another embodiment, the elongated proximal portion 102 may be formed from a first material such as stainless steel (e.g., 304V or 316L stainless steel) or a Ni—Ti alloy and the distal portion may be formed from a second material such as any of the substantially titanium-free Co—Ni—Cr—Mo alloys disclosed herein. In embodiments where the elongated proximal portion 102 and the distal portion 104 are formed from different materials, the elongated proximal portion 102 and the distal portion 104 may joined to one another via a welded, brazed, or adhesive joint 116 that joins the proximal portion 102 and the distal portion 104 into a torque transmitting relationship.

It is worth noting that MP35NLT is a very corrosion resistant alloy and that, under certain conditions, joining MP35NLT to a metal such as stainless steel could lead to galvanic corrosion of the stainless steel. This should not be a problem with guide wires, which are not designed to be implanted in the body for an extended period of time. However, galvanic corrosion could possibly be a problem only if the wire were left in the body for an extended period of time (i.e., days or weeks or longer).

In one embodiment, selected portions of the guide wire device 100 or the entire guide wire device 100 may be processed by cold working one or more of the proximal and distal portions followed by an optional aging step to yield a substantially titanium-free Co—Ni—Cr—Mo alloy having a Young's modulus of at least about 230 GPa, a shear modulus of at least about 80 GPa, and a yield strength of about 1 GPa to about 2 GPa. As discussed elsewhere herein, increasing levels of cold-work followed by aging can affect the Young's and shear moduli to a limited degree and could significantly raise the yield strength of the alloy, but this would come at great expense in terms of ductility in guide wire applications.

In one embodiment, selected portions of the guide wire device 100 or the entire guide wire device 100 may be cold worked to exhibit about 10% to about 95% cold work, about 10%, or about 60% cold work, or about 20% to about 50% cold work. Cold work can be followed by aging at a temperature of at least about 430° C. to about 650° C. for about 30 minutes to about 240 minutes.

Referring again to FIG. 1, the distal portion 104 has at least one tapered section 106 that, in the illustrated embodiment, becomes smaller in the distal direction. The length and diameter of the tapered distal core section 106 can, for example, affect the trackability of the guide wire device 100. Typically, gradual or long tapers produce a guide wire device with less support but greater trackability, while abrupt or short tapers produce a guide wire device that provides greater support but also greater tendency to prolapse (i.e., kink) when steering. The length of the distal end section 106 can, for example, affect the steerability of the guide-wire device 100. In one embodiment, the distal end section 106 is about 10 cm to about 40 cm in length.

The proximal end section 102 of the guide wire device has a diameter of about 0.3 mm to about 1.0 mm. In one embodiment, the tapered distal section can be formed by grinding the distal portion 104 to terminal diameter of diameter of about 0.1 mm to about 0.05 mm to form the very end 108 of the distal tapered end section 106. That is, the tapered end section 106 gradually tapers from a diameter of about 0.3 mm to about 0.5 mm to a terminal diameter of about 0.1 mm to about 0.05 mm at the distal end (e.g., 108) of the guide wire device 100.

In guide wires, which are typically single-use disposable products that are not designed to be in place in the body or implanted in the body for long periods of time, fatigue resistance (i.e., long-term durability) is generally not a concern. However, short-term measures of durability such as the consistency of tensile break load and turns to failure (torsional ductility) are very important. Because the distal tapered end section 106 section is ground to such a small diameter, having sizeable inclusions in this section could adversely impact either of these performance attributes due to the fact that a guide wire's tensile break load and turns to failure values depend primarily on the distal few centimeters that have been ground to the smallest diameter.

In the illustrated embodiment, the tapered distal core section 106 includes the shapeable very distal end section 108, which is shapeable because MP35NLT's yield strength characteristics are similar to stainless steel so it is possible for users to bend the distal end section by hand. As such, shapeable end sections can be integral to the guide wire device 100 as shown, or they can be a separate piece (not shown) that is included as part of the distal end of the guide wire device 100. Having a shapeable very distal end section 108 can allow a practitioner to shape the distal and of the guide wire device 100 to a desired shape (e.g., a J-bend) for tracking through the patient's vasculature.

As illustrated in FIG. 1, the guide wire device 100 includes a helical coil section 110. The helical coil section 110 affects support, trackability, and visibility of the guide wire device and provides tactile feedback. The most distal section of the helical coil section 110 is made of radiopaque metal such as platinum or platinum alloys such as platinum-nickel alloys to facilitate the radiographic observation thereof while it is disposed within a patient's body. As illustrated, the helical coil section 110 is disposed about at least a portion of the distal portion 104 and has a rounded, atraumatic cap section 120 on the distal end thereof. The helical coil section 110 is secured to the distal portion 104 at proximal location 114 and at intermediate location 112 by a suitable technique such as, but not limited to, soldering, brazing, welding, or adhesive.

In one embodiment, portions of the guide wire device 100 are coated with a coating 118 of lubricous material such as polytetrafluoroethylene (PTFE) (sold under the trademark Teflon by du Pont, de Nemours & Co.) or other suitable lubricous coatings such as the polysiloxane coatings, polyvinylpyrrolidone (PVP), and the like.

Figure 2:
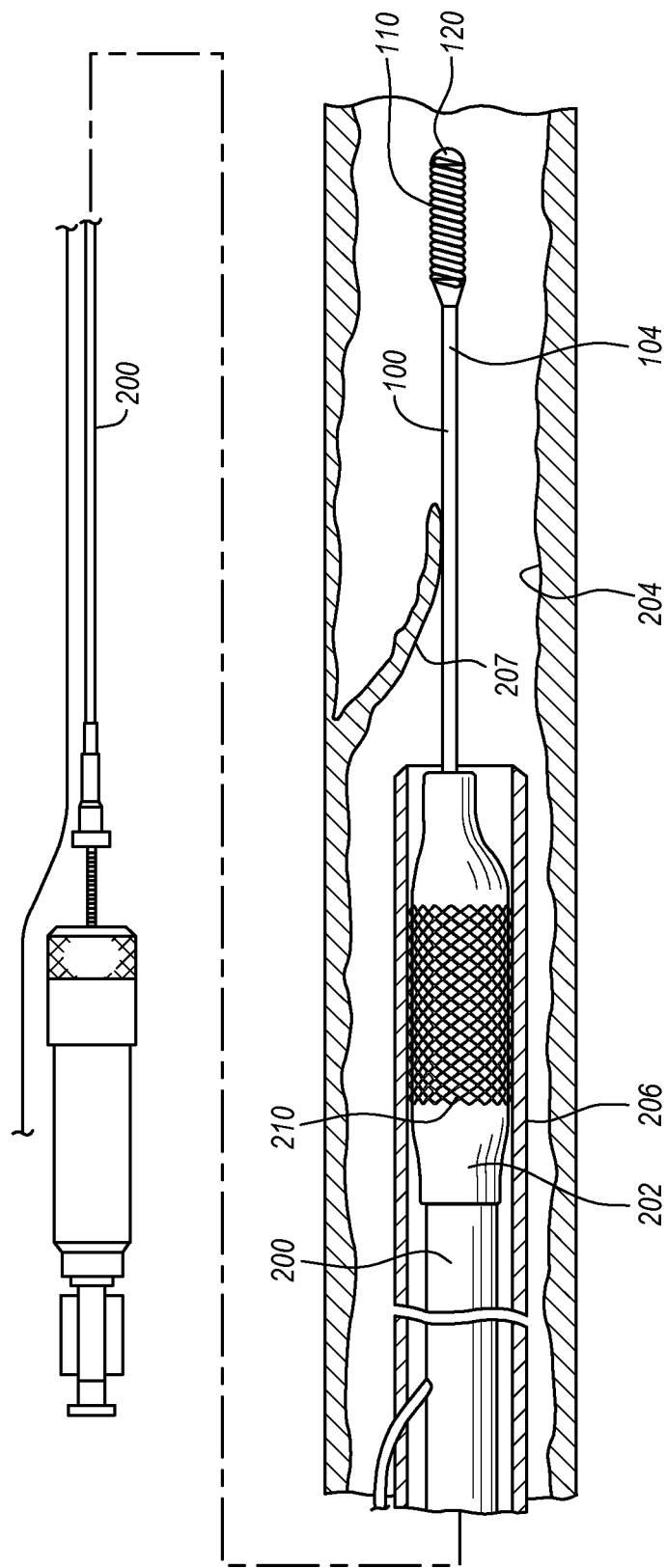
FIG. 2 is a side elevation view, in partial cross-section, of a delivery catheter within a body lumen having a stent disposed about the delivery catheter according to an embodiment of the present disclosure.

Referring now to FIG. 2, the guide wire device 100 is shown configured to facilitate deploying a stent 210. FIG. 2 provides more detail about the manner in which the guide wire device 100 may be used to track through a patient's vasculature where it can be used to facilitate deployment of a treatment device such as, but not limited to the stent 210. FIG. 2 illustrates a side elevation view, in partial cross-section, a delivery catheter 200 having a stent 210 disposed thereabout according to an embodiment of the present disclosure. The portion of the illustrated guide wire device 100 that can be seen in FIG. 2 includes the distal portion 104, the helical coil section 110, and the atraumatic cap section 120. The delivery catheter 200 has an expandable member or balloon 202 for expanding the stent 210, on which the stent 210 is mounted, within a body lumen 204 such as an artery.

The delivery catheter 200 may be a conventional balloon dilatation catheter commonly used for angioplasty procedures. The balloon 202 may be formed of, for example, polyethylene, polyethylene terephthalate, polyvinylchloride, nylon, Pebax™ or another suitable polymeric material. To facilitate the stent 210 remaining in place on the balloon 202 during delivery to the site of the damage within the body lumen 204, the stent 210 may be compressed onto the balloon 202. Other techniques for securing the stent 210 onto the balloon 202 may also be used, such as providing collars or ridges on edges of a working portion (i.e., a cylindrical portion) of the balloon 202.

In use, the stent 210 may be mounted onto the inflatable balloon 202 on the distal extremity of the delivery catheter 200. The balloon 202 may be slightly inflated to secure the stent 210 onto an exterior of the balloon 202. The catheter/stent assembly may be introduced within a living subject using a conventional Seldinger technique through a guiding catheter 206. The guide wire 100 may be disposed across the damaged arterial section with the detached or dissected lining 207 and then the catheter/stent assembly may be advanced over the guide wire 208 within the body lumen 204 until the stent 210 is positioned at the target location 207. The balloon 202 of the catheter 200 may be expanded, expanding the stent 210 against the interior surface defining the body lumen 204 by, for example, permanent plastic deformation of the stent 210. When deployed, the stent 210 holds open the body lumen 204 after the catheter 200 and the balloon 202 are withdrawn.

III. Methods for Fabricating a Guide Wire Device

In another embodiment, a method for fabricating a guide wire device is disclosed. The method includes (1) fabricating an elongate guide wire member having a proximal section and a distal section, wherein at least one of the proximal section or the distal section is fabricated from any of the substantially titanium-free Co—Ni—Cr—Mo alloys disclosed herein and (2) grinding the distal end section to a distally tapered cross sectional diameter of about 0.1 mm to about 0.05 mm. The method further includes (3) disposing a helical coil section about at least a distal end portion of the distal section, (4) joining the helical coil to the elongate guide wire member at a proximal location, (5) forming a rounded cap section on a distal end of the helical coil, and (6) applying at least one lubricious outer coating layer over at least a portion of the elongate guide wire member to form the guide wire device.

To form the substantially titanium-free Co—Ni—Cr—Mo alloy, each of the four principal elements (i.e., cobalt, nickel, chromium, and molybdenum) can be refined to form a furnace charge stock that is substantially free of titanium and other contaminating elements. The refined principal elements are combined in an alloy melt by vacuum induction melting. Homogenization and final refining is performed in a vacuum arc refining furnace. The Co—Ni—Cr—Mo alloy material produced in this way typically contains less than 0.05 wt % titanium, less than about 0.01 wt % titanium, less than about 0.005 wt % titanium, or less than about 0.001 wt % titanium in comparison to conventionally processed MP35N, which contains up to 1.0% titanium by weight.

After vacuum arc refining and cooling, MP35NLT can be processed into wire for forming a guide wire core by conventional cold processing methods including one or more of drawing, swaging, cold rolling, stamping, extrusion, forging, and other cold processing methods known to persons having skill in the art. Cold working the MP35NLT alloy using processes such as those listed herein can yield significant increases in strength (see, e.g., Table 3). In one embodiment, the MP35NLT alloy has a yield strength of about 1 GPa to about 2.3 GPa imparted by at least about 10% to about 95% cold work. Preferably, the MP35NLT alloy includes about 10% to about 60% cold work or about 20% to about 50% cold work.

For further increases in yield strength, the cold worked alloy can be precipitation hardened or "aged" by heat treating the alloy at a temperature of at least about 430° C. to about 650° C. for about 30 minutes to about 240 minutes. However, at the high levels of prior cold work needed to provide high yield strengths in guide wire applications, deliberate age hardening of MP35N or MP35NLT can lead to severe loss of ductility and is thus not generally recommended.

In one embodiment, the methods disclosed herein further include (a) fabricating the distal section of the elongate guide wire member from the Co—Ni—Cr—Mo alloy, (b) cold working at least a portion of the Co—Ni—Cr—Mo alloy to yield a cold worked section that exhibits at least about 50% cold work.

In another embodiment, the methods disclosed herein include (a) fabricating the proximal and distal sections of the elongate guide wire member from any of the substantially titanium-free Co—Ni—Cr—Mo alloys disclosed herein, (b) cold working at least a portion of the Co—Ni—Cr—Mo alloy to yield a cold worked section that exhibits at least about 80% cold work.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A guide wire device, comprising:
an elongate guide wire member having a proximal end section and a distal end section,
wherein at least the distal end section of the elongate guide wire member is fabricated from a cobalt-nickel-chromium-molybdenum (Co—Ni—Cr—Mo) alloy that comprises less than 0.05% titanium by weight, wherein the distal end section has higher Young's and shear moduli and greater yield strength as compared to the proximal end section as imparted by 50% to 95% cold work.

2. The guide wire device of claim 1, wherein the proximal end section is fabricated from a stainless steel alloy, the distal end section is fabricated from the Co—Ni—Cr—Mo alloy, and the proximal end section and the distal end section are joined to one another by one or more of a welded joint, a brazed joint, or an adhesive joint.

3. The guide wire device of claim 1, wherein the proximal end section and the distal end section are fabricated from the Co—Ni—Cr—Mo alloy.

4. The guide wire device of claim 1, wherein the Co—Ni—Cr—Mo alloy comprises less than 0.001 wt % titanium.

5. The guide wire device of claim 1, wherein the Co—Ni—Cr—Mo alloy comprises:
- 31.5 wt % to 39 wt % cobalt;
- 33 wt % to 37 wt % nickel;
- 19 wt % to 21 wt % chromium;
- 9 wt % to 10.5 wt % molybdenum; and
- less than 0.05 wt % titanium.

6. The guide wire device of claim 5, wherein the Co—Ni—Cr—Mo alloy comprises less than 0.001 wt % titanium.

7. The guide wire device of claim 1, wherein the proximal end section has a first cross sectional dimension and the distal end section has a ground surface defining a second, smaller cross sectional dimension and a distally tapered section disposed between the proximal and distal end sections.

8. The guide wire device of claim 7, wherein the proximal end section has a cross sectional diameter of 0.3 mm to 1 mm and the ground surface at the distal end section has a cross sectional diameter of 0.1 mm to 0.05 mm.

9. The guide wire device of claim 1, wherein the distal end section has a tapered profile defined by a ground surface ground to a diameter of 0.1 mm to 0.05 mm.

10. A guide wire device, comprising:
- an elongate guide wire member having a proximal end section and a distal end section,
- wherein the distal end section has higher Young's and shear moduli and greater yield strength as compared to the proximal end section,
- wherein the distal end section of the elongate guide wire member is fabricated from a cobalt-nickel-chromium-molybdenum (Co—Ni—Cr—Mo) alloy that comprises less than 0.05% of titanium by weight, the Co—Ni—Cr—Mo alloy having a Young's modulus of at least 230 GPa, a shear modulus of at least 80 GPa, and a yield strength of 1 GPa to 2 GPa imparted by at least 50% to 95% cold work, and
- wherein the proximal end section is fabricated from a stainless steel alloy, and the proximal end section is joined to the distal end section by one or more of a welded joint, a brazed joint, or an adhesive joint.

11. The guide wire device of claim 10, wherein the Co—Ni—Cr—Mo alloy comprises:
- 31.5 wt % to 39 wt % cobalt;
- 33 wt % to 37 wt % nickel;
- 19 wt % to 21 wt % chromium;
- 9 wt % to 10.5 wt % molybdenum; and
- less than 0.05 wt % titanium.

12. The guide wire device of claim 11, wherein the Co—Ni—Cr—Mo alloy comprises less than 0.001 wt % titanium.

13. The guide wire device of claim 10, wherein the Co—Ni—Cr—Mo alloy exhibits 80% to 95% cold work.

14. The guide wire device of claim 10, wherein the proximal end section has a cross sectional diameter of 0.3 mm to 0.5 mm and the distal end section has a ground surface defining a second, smaller cross sectional dimension with a distal taper section having a cross sectional diameter of 0.1 mm to 0.05 mm.

* * * * *